US00PP20408P2

(12) United States Plant Patent
Ault

(10) Patent No.: US PP20,408 P2
(45) Date of Patent: Oct. 13, 2009

(54) ***BAPTISIA* PLANT NAMED 'SOLAR FLARE'**

(50) Latin Name: *Baptisia hybrid*
Varietal Denomination: Solar Flare

(76) Inventor: James R. Ault, Chicago Botanic Garden, 1000 Lake Cook Rd., Glencoe, IL (US) 60022

( * ) Notice: Subject to any disclaimer, the term of this patent is extended or adjusted under 35 U.S.C. 154(b) by 0 days.

(21) Appl. No.: 12/229,798

(22) Filed: Aug. 27, 2008

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Susan B McCormick Ewoldt
(74) *Attorney, Agent, or Firm*—Penny J. Aguirre

(57) ABSTRACT

A new cultivar of interspecific *Baptisia*, 'Solar Flare', characterized by its upright primary racemes and its spreading secondary racemes of flowers that are initially yellow in color and age to yellow with a distinct orange-violet cast, its stems that emerge with a purple cast in spring, its lack of foliage on the lower 25 to 40 cm of stem, its broad rounded plant habit, and its vigorous growth habit.

3 Drawing Sheets

Botanical classification: *Baptisia* hybrid.
Cultivar designation: 'Solar Flare'.

BACKGROUND OF THE INVENTION

The present invention relates to a new and distinct cultivar of hybrid *Baptisia* plant, botanically known as *Baptisia* 'Solar Flare' and will be referred to hereafter by its cultivar name, 'Solar Flare'. The new cultivar represents a new false indigo, an herbaceous perennial grown for landscape use.

The new invention arose from an ongoing breeding program in a dedicated test plot in Glencoe, Ill. There are approximately 17 species of *Baptisia* that are native to North America, many of which have highly ornamental flowers and foliage and excellent adaptability to garden cultivation. The breeding program was established in 1995 with the goal of developing novel interspecific *Baptisia* hybrids with unique and superior garden attributes.

'Solar Flare' was selected as a single unique plant by the inventor in 2004 in Glencoe, Ill. after evaluating seedlings that derived from open-pollination of an unnamed plant of hybrid *Baptisia* (*Baptisia tinctoria*×*Baptisia alba*) in 2000. The pollen parent is unknown.

Asexual reproduction of the new cultivar was first accomplished by stem cuttings in August of 2003 in Glencoe, Ill. by the inventor. The characteristics of this cultivar have been determined to be stable and are reproduced true to type in successive generations.

SUMMARY OF THE INVENTION

The following traits have been repeatedly observed and represent the characteristics of the new cultivar as observed for five years in Glencoe, Ill. These attributes in combination distinguish 'Solar Flare' as unique from other varieties of *Baptisia* known to the Inventor.

1. 'Solar Flare' produces racemes of flowers that are initially yellow in color and age to yellow with a distinct orange-violet cast.
2. The newly emerging vegetative stems of 'Solar Flare' have a distinct purple cast in early spring.

3. 'Solar Flare' produces both primary and secondary inflorescences.
4. 'Solar Flare' has a broad, rounded plant habit with upright primary stems and spreading secondary stems.
5. 'Solar Flare' has no foliage on the lowermost 25 to 40 cm of the stem.
6. 'Solar Flare' has a vigorous growth habit and was selected in part for its vigor in comparison to its siblings.

In comparison to the female parent, an unnamed plant of *Baptisia tinctoria*×*Baptisia alba*, 'Solar Flare' has yellow colored flowers that mature with a orange to violet case whereas the female parent has violet colored flowers. The female parent is also different in having a vase-shaped habit and newly emerging stem that are green in color without the purple cast that is observed with 'Solar Flare'. 'Solar Flare' can be compared to *Baptisia sphaerocarpa*, a species that also exhibits yellow flowers at anthesis. *Baptisia sphaerocarpa* differs in having flowers that remain golden yellow in color for the duration of bloom and lack any orange violet cast, in having green stems without a purple case, and in having stems that are shorter with foliage most of the way to the base. 'Solar Flare' can also be compared to *Baptisia* 'Midnight' (U.S. Plant patent application Ser. No. 12/229,873), which is similar in producing upright stems without foliage on the lower 20 to 40 cm of the stem and in producing secondary inflorescences. 'Midnight' differs in having flowers that are violet-blue color, in having green stems that lack a purple cast in the spring, and in having a more vase-shaped plant habit.

BRIEF DESCRIPTION OF THE DRAWING

The accompanying colored photographs illustrate the overall appearance and distinct characteristics of the new *Baptisia*. The three photographs were taken of plants five, three, and five years, respectively, in age as grown outdoors in a trial plot in Glencoe, Ill.

The photograph in FIG. 1 is a side view of a plant of 'Solar Flare' in bloom and illustrates the plant habit and flowering habit in full bloom.

Figure 1:
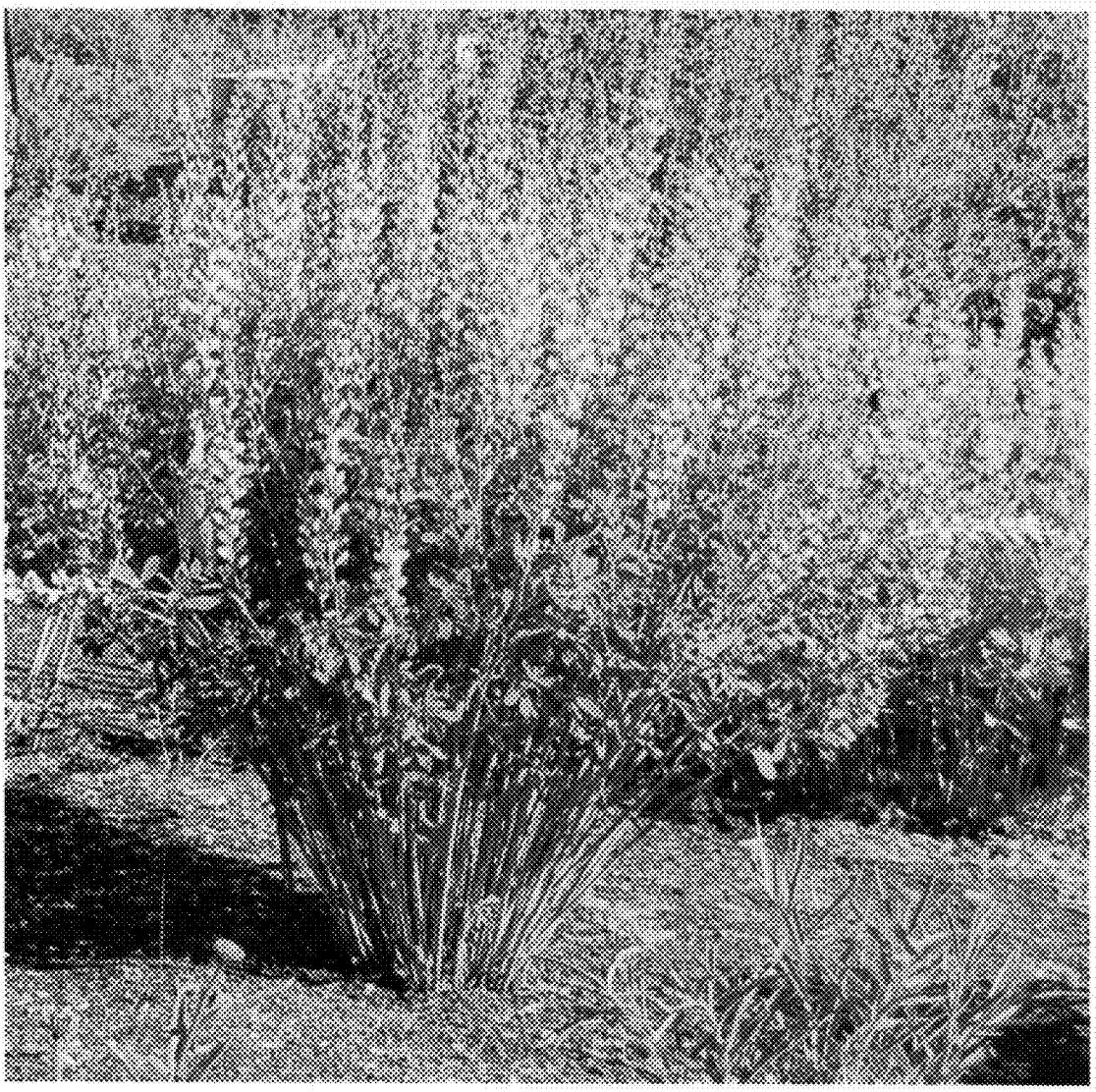
Figure 2:
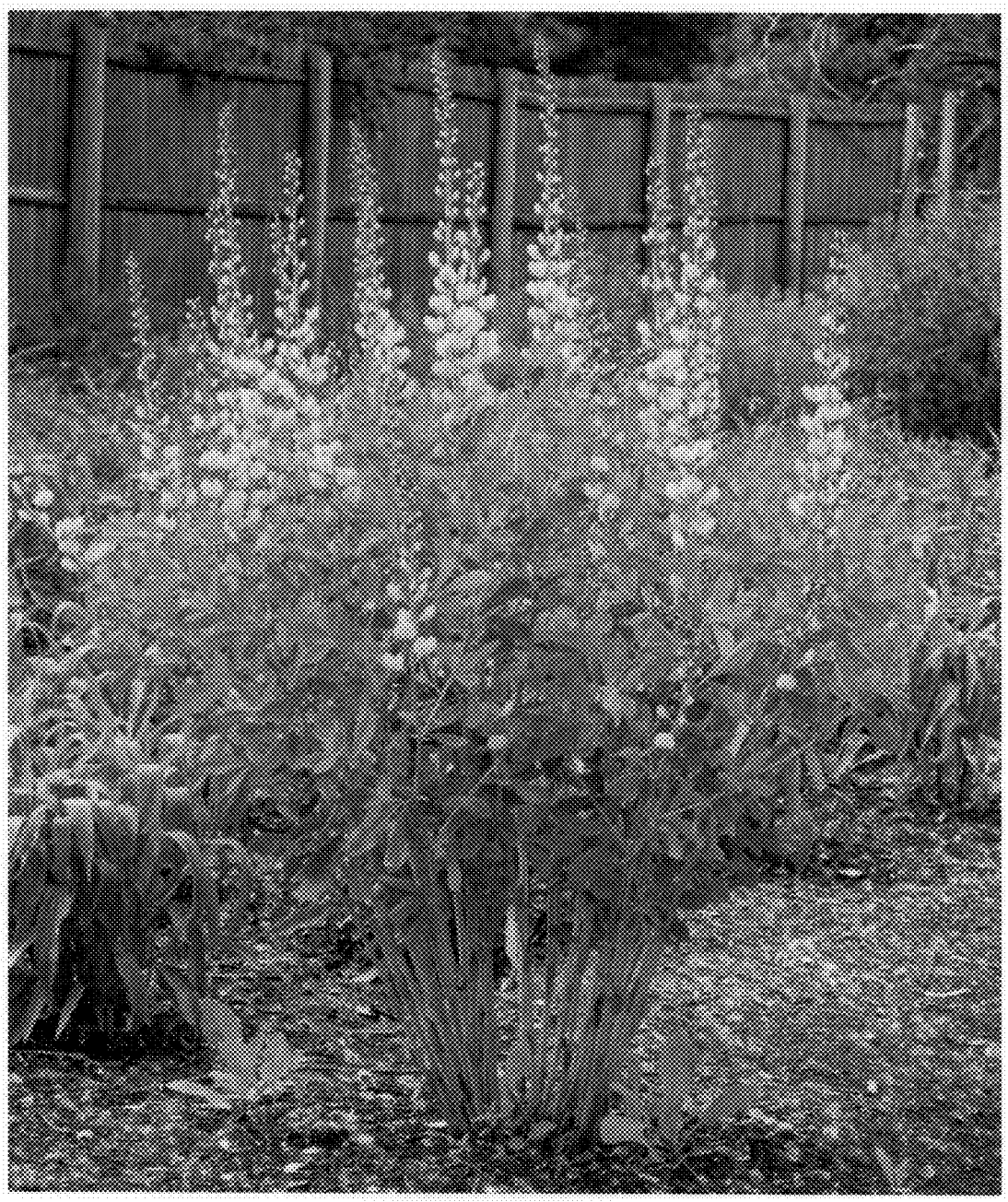

The photograph in FIG. 2 provides of side view of a plant of 'Solar Flare' in bloom with the secondary inflorescences just starting to bloom.

Figure 3:
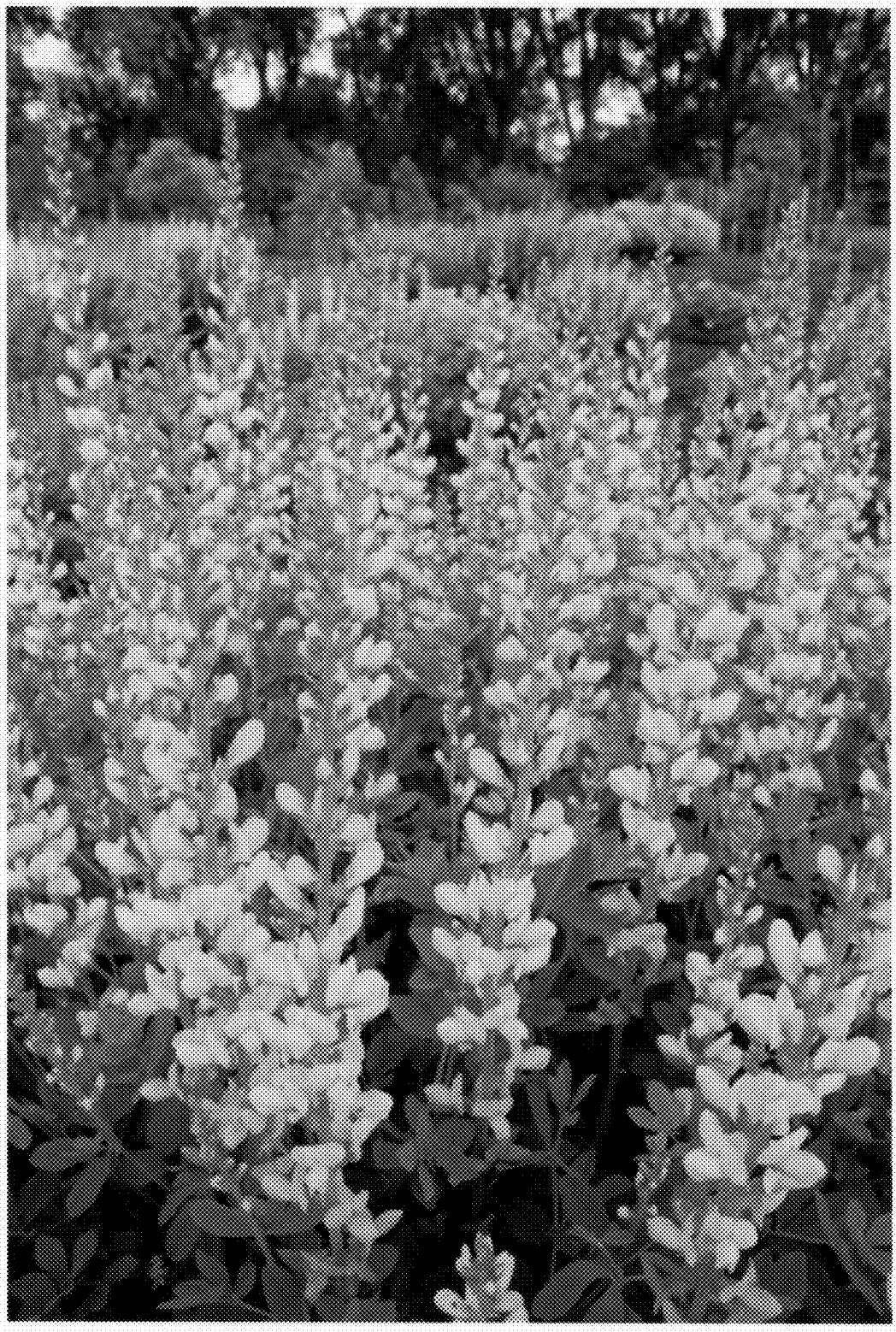

The photograph in FIG. 3 provides a close up view of the flowers of 'Solar Flare'. The colors in the photographs are as close as possible with the photographic and printing technology utilized. The color values cited in the detailed botanical description accurately describe the colors of the new *Baptisia*.

DETAILED BOTANICAL DESCRIPTION OF THE PLANT

The following is a detailed description of 6 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming peroid.*—2 weeks or greater in mid June Glencoe, Ill.

*Plant habit.*—Perennial, broad mounded plant habit with upright to spreading stems.

*Height and spread.*—Reaches about 1.5 m in width and 1.25 m in height (in bloom).

*Hardiness.*—U.S.D.A. Zones 4 to 8.

*Culture.*—Prefers well drained to medium moist soils in full sun, tolerant to lean soils and drought.

*Diseases.*—No susceptibility or resistance to diseases has been observed.

*Root description.*—Deep rooted, fibrous.

Growth and propagation:

*Propagation.*—Stem cuttings.

*Growth rate.*—Vigorous relative to other *Baptisia*.

Stem description:

*Branch habit.*—Average of 3 primary branches, typically 1 to 2 secondary branches, and 1 to 2 tertiary branches, primary stems upright-spreading with secondary stems more lax resulting in a broad-rounded plant habit.

*Stem size.*—Reach about 125 cm in length (including raceme), average of 5 to 7 mm in width (about 1 cm at base and 3 mm at apex of lateral branches).

*Stem shape.*—Oval.

*Stem color.*—144A to 144B when mature, in spring the stems are flushed with N77A.

*Stem surface.*—Hairless, satiny but slightly glaucous, finely ribbed.

Foliage description:

*Leaf shape.*—Fan-shaped in overall outline.

*Leaf division.*—3-palmate.

*Leaf internode.*—Varies from about 15 to 18 cm from base of laterals branch to 3 to 8 cm on tertiary branches.

*Leaf size.*—About 4 to 6.5 cm in length and 4 to 9 cm in width (across all three leaflets) when mature.

*Leaf quantity.*—About 12 to 17 per lateral branch with no foliage on the lower 25 to 40 cm of stem.

*Leaflet shape.*—Oblanceolate.

*Leaflet base.*—Between cuneate and attenuate.

*Leaflet apex.*—Acute to rounded.

*Leaflet venation.*—Pinnate pattern, not conspicuous, color matches leaflet color on the upper and lower surface with the mid rib of lower surface 144B.

*Leaflet margins.*—Entire.

*Leaf attachment.*—Petiolate.

*Leaf arrangement.*—Alternate.

*Leaflet surface.*—Glaucous on upper and lower surface.

*Leaflet color.*—Newly expanded; upper and lower surface 144A to 137B, mature; upper; and lower surface 137A.

*Leaflet size.*—Up to about 6.5 cm in length, up to about 2.5 cm in width.

*Petioles.*—Average of 4 mm in length and 2 mm in width, clasping to stem at mature nodes, between 144A and 144B in color, surface is hairless and satiny.

*Stipules.*—Lanceolate in shape, base is truncate to stem, apex is narrowly acute to acuminate, average of 1.5 cm in length and 5 mm in width but varies from minute on newly formed leaves to 3 cm in length and 7 mm in width on basal nodes, 137B in color on upper and lower surface.

Flower description:

*Inflorescence type.*—Terminal and axillary racemes of papilionaceous flowers, blooms from the base to the apex.

*Inflorescence size.*—Terminal inflorescences up to 40 cm in length and 4.5 cm in width, axillary inflorescences up to 10 cm in length.

*Lastingness of inflorescence.*—Terminal inflorescences last 12–16 days with axillary inflorescences lasting 6–8 days.

*Blooming period.*—Two-plus weeks in early to mid June in Glencoe, Ill., USA.

*Flower size.*—About 2 cm in depth and about 1.5 cm in diameter.

*Flower fragrance.*—None.

*Flower number.*—About 35 to 40 on terminals, about 8 to 12 on axillary branches.

*Peduncle.*—Oval in shape, up to 40 cm in length and ranges from 1.0 cm in width at the base of the inflorescence to 2 mm in width at the apex, 144A to 144B in color, surface is hairless, satiny but slightly glaucous, and finely ribbed, flower internode length ranges from 5 mm to 4 cm with an average of 1 cm.

*Petiole.*—About 5 mm in length, about 1.5 mm in width, oval in shape, 144A to 144B in color with blush of N77A near apex, satiny surface.

*Flower buds.*—Reniform, about 2 cm in length and 7 mm in width, 1A in color, calyx portion same as open flowers.

*Flower type.*—Papilionaceous, held at about a 45° angle.

*Calyx.*—Campanulate, about 6 mm in length and 5 mm in diameter, surface is slightly glaucous, 144A in color with a few flecks of N77A, persistent.

*Sepals.*—5, fused with the exception of apex of each, free portion is triangular in shape 4 mm in width and 3 mm in depth with an acute apex, 144A in color with a few flecks of N77A.

*Corolla features.*—Papilionaceous (4 segments) with a keel, an inner lip and 2 lateral wings, the inner lip; comprised of two lobes that are folded around stamens and pistil, lobes are reniform in shape, about 1.5 cm in length and 8 mm in width, rounded apex, lateral wings; loosely surround inner lip, oblong in shape, about 1.8 cm in length and 8 mm in width, rounded apex, keel; reflexed, orbicular in shape with cordate apex, about 1.7 cm in length and width, all segments; glabrous in texture, entire margin, base is rounded with a short attenuated section on keel and oblique with an attenuated section on other segments, color open 1A (yellow) and become flushed with N77C (purple) as they mature giving an overall effect of yellow colored flowers at the apex to flowers at the base that are yellow with a violet to orange cast.

*Receptacle.*—Disk-shaped, gelatinous, 144A in color, about 3 mm in diameter and 1.2 mm in depth.

Reproductive organs:

*Gynoecium.*—1 Pistil, about 1.8 cm in length, 1.5 mm in width; style is 1 cm in length, <1 mm in width, and 143C in color; stigma minute, too small to color read; ovary is superior with a stipe 3 mm in length, 143C in color, 5 mm in length and 1.5 mm in width; stipe is 138D in color, 3 mm in length and <1 mm in width.

*Androcoecium.*—10 stamens, not united, 1.6 cm in length and 1 mm in width; filament is 1.5 cm in length, 1 mm in width and 145C in color; anther is dorsifixed, 1 mm in length and <1 mm in width and completely covered with pollen, pollen is abundant and 17A in color.

*Fruit and seed.*—An inflated pod, technically a legume, globose-oblong in shape, average of 2.5 cm in length and 1 cm in width; each with a beak about 9 mm in length, emerges green, 144B to 144C and matures in August to an irregular blend of 200A and N199C, walls about 1.5 mm in thickness and woody at maturity, seed; average of 2 per fruit (open-pollinated), 200A blended with N199B in color, oval with the hilum side more or less straight, seed compressed to flattish, about 4 mm long × 3 mm wide × 1.3 mm in thickness.

It is claimed:

1. A new and distinct cultivar of *Baptisia* plant named 'Solar Flare' as herein illustrated and described.

* * * * *